United States Patent [19]

Hikawa et al.

[11] Patent Number: 4,543,119

[45] Date of Patent: Sep. 24, 1985

[54] METHOD FOR PROMOTING CROP GROWTH

[75] Inventors: Masanori Hikawa, Osaka; Ippei Toyoda, Urayasu, both of Japan

[73] Assignee: Nihon Nohyaku Co., Ltd., Tokyo, Japan

[21] Appl. No.: 460,792

[22] Filed: Jan. 25, 1983

[30] Foreign Application Priority Data

Feb. 1, 1982 [JP] Japan .................................. 57-14535

[51] Int. Cl.$^4$ ............................................ A01N 43/02
[52] U.S. Cl. ............................................................ 71/90
[58] Field of Search ......................... 71/77, 90; 424/277

[56] References Cited

U.S. PATENT DOCUMENTS

| | | | |
|---|---|---|---|
| 3,678,074 | 7/1972 | Nikles | 71/90 |
| 3,761,596 | 9/1973 | Taninaka et al. | 424/277 |
| 3,864,115 | 2/1975 | Schrader et al. | 71/77 |
| 3,876,663 | 4/1975 | Taninaka et al. | 424/277 |
| 4,101,307 | 7/1978 | Clapot et al. | 71/90 |
| 4,187,096 | 2/1980 | Rasheed et al. | 71/90 |
| 4,265,655 | 5/1981 | Farooq | 71/90 |

FOREIGN PATENT DOCUMENTS

| | | | |
|---|---|---|---|
| 49-30529 | 3/1974 | Japan | 424/277 |
| 49-35272 | 9/1974 | Japan | 71/90 |
| 53-03519 | 1/1978 | Japan | 424/277 |

*Primary Examiner*—Glennon H. Hollrah
*Assistant Examiner*—Raymond Covington
*Attorney, Agent, or Firm*—Oblon, Fisher, Spivak, McClelland & Maier

[57] ABSTRACT

There is provided a method of promoting crop growth by the use of a compound which has been known as insecticide and fungicide and which is represented by the formula,

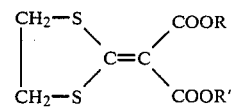

wherein R and R' may be same or different and are lower alkyl or allyl group. The compound is applied to soil surface or incorporated into soil in an amount of more than 500 g per 10 ares to promote growth of crops such as strawberry, eggplant, tea plant, soybean and others.

3 Claims, No Drawings

METHOD FOR PROMOTING CROP GROWTH

The present invention relates to method for promoting crop growth, which comprises applying to soil surface or incorporating into soil an effective amount of compounds represented by the formula (I):

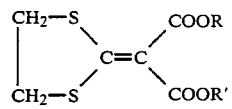

(I)

wherein R and R', which may be same or different, are individually a lower alkyl group or an allyl group.

The compounds represented by the formula (I) have been known as agricultural and horticultural fungicide which are particularly effective against rice blast, further as insecticide and miticide which are particularly effective against planthopper, as shown in Japanese Patent Publications No. 34126/72, No. 6207/76, No. 9804/76, No. 12687/76, No. 4609/77 and No. 5574/77, and in Japanese Patent Application Kokai No. 3519/78 and No. 28821/79.

Furthermore, the compound represented by the formula (I), wherein R and R' are isopropyl group, has been known as common name "ISOPROTHIOLANE" and has been widely used as a rice blast control agent since 1975. In the course of the study on the effect of the compounds represented by the formula (I) to crop root, it was observed and clarified that the growth of root, particularly root hair was promoted by the application of these compounds to root portion, resulting in the promotion of crop growth. The present invention is based on the finding mentioned above.

The compounds represented by the formula (I) are shown in the following table.

In the formula (I)

$$\begin{array}{c} CH_2-S \\ | \\ CH_2-S \end{array} C=C \begin{array}{c} COOR \\ \\ COOR' \end{array}$$

| Compound No. | R | R' | Melting point or boiling point (m.p.) (b.p.) |
|---|---|---|---|
| 1 | CH₃ | CH₃ | m.p. 64–66° C. |
| 2 | C₂H₅ | C₂H₅ | m.p. 48–49° C. |
| 3 | n-C₃H₅ | n-C₃H₇ | b.p. 168–169° C./0.3 mmHg |
| 4 | i-C₃H₇ | i-C₃H₇ | m.p. 50–51° C. |
| 5 | n-C₄H₉ | n-C₄H₉ | b.p. 177–183° C./0.25 mmHg |
| 6 | t-C₄H₉ | t-C₄H₉ | m.p. 91–92° C. |
| 7 | C₂H₅ | i-C₃H₇ | m.p. 37–39° C. |
| 8 | C₂H₅ | sec-C₄H₉ | b.p. 175–179/0.2 mmHg |
| 9 | CH₂CH=CH₂ | CH₂CH=CH₂ | b.p. 171–174° C./0.2 mmHg |

In order to ascertain the effect of this invention, the compounds represented by the formula (I) may be applied to soil surface or incorporated into soil at growing period and at before or after transplanting of crops, using suitable formulation such as granules, emulsifiable concentrates or wettable powders. In applying the compounds, it is suitable to apply the compounds at 500 g–5000 g per 10 ares in one application. But the dose may be suitably changed according to various factors such as kinds of crops, application time, soil condition or application methods. In case of vegetables such as leafy and root vegetables, the compounds represented by the formula (I) may be applied to soil surface or incorporated into soil at more than 500 g per 10 ares before seeding or planting or at early growth period of the crops.

In case of perennial crops such as tea plant or mulberry trees, the compounds may be applied to soil surface or incorporated into soil at the amount of 1000 g–5000 g per 10 ares, to plant foot or to interrow spacing after final plucking.

In case of tubers such as potatoes or sweet potatoes, beans such as soybean, adjuki bean or peanut, the compounds may be applied in the same method as in the above vegatables.

It is important that roots should be contact with the compounds not to excessive degree to cause phytotoxicity, because the effect of the present invention can be recognized through the effect of the compounds to crop roots.

The compounds can be used in combination with other objective compounds such as pesticides or fertilizers.

The following test examples and formulations examples illustrate concretely this invention, but the invention is not only to be limited to these examples. The examples can be suitably changed factors such as carriers, surface active agent, adjuvants, application dose, application period, application method and kinds of crops.

TEST EXAMPLE 1

100 g of wettable powder containing 50% of compound No. 4 was diluted to 100 times with water.

On 2 months after strawberry seedlings (variety: dunner) were transplanted in the field, the diluted solution containing compound No. 4 was applied stripedly to soil surface in interrow spacing at 100, 500, 1000 and 2000 g per 10 ares. The growth condition of strawberry seedlings such as weed control or fertilization was the same between treated and untreated plot. On 2 and 3 months after the application, weight of root and shoot was examined, comparing treated and untreated plot. Values of each plot was indicated as the average of 10 hills which were sampled randomly. The untreated plot was applied the same amount of carriers without active ingredient. One plot size was 0.5 are.

The results are shown in the following Table 1.

TABLE 1

| | Dose g/10a | After 2 months | | After 3 months | |
| | | Weight of root/hill g | Weight of shoot/hill g | Weight of root/hill g | Weight of shoot/hill g |
|---|---|---|---|---|---|
| Treatment (plot) | 100 | 10 | 16 | 18 | 21 |
| | 500 | 16 | 19 | 22 | 23 |
| | 1000 | 19 | 21 | 26 | 25 |
| | 2000 | 20 | 24 | 28 | 27 |
| Untreatment (plot) | — | 11 | 15 | 16 | 21 |

TEST EXAMPLE 2

Soil (clay loam), which was mixed with 15% granule of compound No. 2 at 100 to 2000 g per 10 ares, was filled in seedling pot (25 cm of diameter and 30 cm of depth) wherein eggplant seedling were transplanted. Seedlings were grown in the greenhouse under fixed temperature and humidity condition. On 20 and 40 days after transplanting, the weight of root and shoot were examined and indicated as average values of 10 pots in 25 pots. The untreated plot was applied the same amount of carriers without active ingredient.

The result is shown in Table 2.

TABLE 2

|  | Dose g/10a | After 20 days | | After 40 days | |
|---|---|---|---|---|---|
|  |  | Weight of root/hill g | Weight of shoot/hill g | Weight of root/hill g | Weight of shoot/hill g |
| Treatment (plot) | 100 | 9 | 24 | 14 | 57 |
|  | 500 | 11 | 27 | 28 | 63 |
|  | 1000 | 13 | 29 | 35 | 67 |
|  | 2000 | 15 | 29 | 39 | 59 |
| Untreatment (plot) | — | 8 | 23 | 15 | 56 |

TEST EXAMPLE 3

After plucking the second leaf of tea plant (variety: Yabukita, nine years old) on September 17, 15% granule of compound No. 7 was applied to interrow spacing and hill to examine the effect to first crop tea leaf in the next year (April 30). One plot size was 5 ares with 5 replicates. The value was indicated as the average of 3 places where tests were carried out. To the untreated plot was applied the same amount of carriers without active ingredient. Another condition was the same between treated and untreated plot.

The result is shown in Table 3.

TABLE 3

|  | Dose g/10a | Shoot | Developed shoot | Undeveloped shoot | Total weight g |
|---|---|---|---|---|---|
| treatment (plot) | 1500 | 129 | 66 | 63 | 65 |
|  | 3000 | 137 | 85 | 52 | 67 |
|  | 5000 | 121 | 28 | 93 | 64 |
| untreatment (plot) | — | 90 | 22 | 68 | 51 |

TEST EXAMPLE 4

15% granule of compound No. 4 was incorporated into soil at 5, 15, 30 and 100 kg per ares before soybean seeding, May 20. One plot size was 1 are with 2 replicates. On November 2, soybeans were harvested and examined yield. The untreated plot was applied the same amount of carriers without active ingredient. Another condition was the same between treated and untreated plot.

The result is shown in Table 4.

TABLE 4

|  |  | Dose g/10a | Shoot | Pod | Grain | Grain weight g |
|---|---|---|---|---|---|---|
| Treatment (plot) | The present invention | 600 | 16.4 | 321.1 | 588.7 | 134.3 |
|  |  | 1,800 | 15.1 | 337.0 | 633.3 | 134.3 |
|  |  | 3,600 | 16.2 | 326.5 | 575.2 | 123.3 |
|  |  | 12,000 | 14.6 | 263.0 | 461.9 | 99.4 |
| Untreatment (plot) |  | — | 15.0 | 281.3 | 512.1 | 109.0 |

Also, the growth promoting effect shown above is recognized in another crops, for example, vegetables such as cabbage, cucumber, tomato, spanish paprika or spinach: tubers such as potato or sweet potato: leguminous plant such as soybean, adzuki bean or kidney bean: gramineous crops such as barley, wheat or corn: forage crops such as clover or italian ryegrass.

FORMULATION EXAMPLE 1

A wettable powder composition obtained by uniformly mixing and grinding the following constituents.
Compound No. 4: 50 parts
Mixture of diatomaceous earth and clay: 45 parts
Polyoxyethylene nonylophenyl ether: 5 parts

FORMULATION EXAMPLE 2

A granule composition obtained by uniformly mixing and grinding the following constituents, kneading the mixture with a suitable amount of water, making extrusion-granulation the mixture by wire netting equipped with a suitable network, drying and making uniform the grain size to 14–32 meshes.
Compound No. 2: 15 parts
Mixture of Talc and Clay: 80.5 parts
Calcium liguninsulfonate: 4 parts
Nonionic surface active agent: 0.5 parts

FORMULATION EXAMPLE 3

A granule composition obtained by uniformly mixing and grinding the following constituents, kneading the mixture with a suitable amount of water, making extrusion granulation the mixture by wire netting equipped with a suitable network drying and making uniform the grain size to 14–32 meshes.

What we claim is:

1. A method for promoting crop growth, which comprises applying to the soil an effective amount of a compound represented by the formula (I):

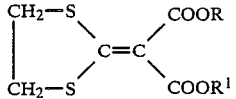

wherein R and R$^1$, which are the same or different, are each a lower alkyl group, whereby the crop growth is effected by root growth stimulation.

2. The method according to claim 1, wherein the amount applied is 500 g–5000 g per 10 ares.

3. A method for promoting the growth of cabbage, cucumber, tomato, spanish paprika, eggplant, potato, sweet potato, soybean, adzuki bean, kidney bean, barley, wheat, corn, clover, italian ryegrass, strawberry and tea, which comprises applying to the soil 500 to 5000 g per 10 ares of a compound represented by the formula (I):

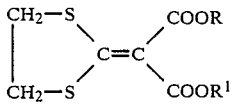

wherein R and R$^1$, which are the same or different, are each a lower alkyl group, whereby the crop growth is effected by root growth stimulation.

* * * * *